United States Patent [19]

Gibson

[11] Patent Number: 5,060,633

[45] Date of Patent: Oct. 29, 1991

[54] LARYNGOSCOPE BLADE

[76] Inventor: Michael S. Gibson, 22733 Margarita Dr., Woodland Hills, Calif. 91364

[21] Appl. No.: 577,188

[22] Filed: Aug. 31, 1990

[51] Int. Cl.$^5$ ............................................... A61B 1/06
[52] U.S. Cl. ........................................ 128/11; 128/16
[58] Field of Search .................................... 128/9–11, 128/15, 16, 18; 362/208

[56] References Cited

U.S. PATENT DOCUMENTS

| | | | |
|---|---|---|---|
| 2,493,205 | 1/1950 | Muldoon | 362/208 |
| 3,826,248 | 7/1974 | Gobels | 128/11 |
| 3,856,001 | 12/1974 | Phillips | 128/11 |
| 4,273,112 | 6/1981 | Heine et al. | 128/11 |
| 4,592,343 | 6/1986 | Upsher | 128/11 |
| 4,884,558 | 12/1989 | Gorski et al. | 128/11 |
| 4,901,708 | 2/1990 | Lee | 128/16 |

Primary Examiner—Stephen C. Pellegrino
Assistant Examiner—Ralph A. Lewis
Attorney, Agent, or Firm—Herbert W. Larson

[57] ABSTRACT

A laryngoscope blade having a self contained base housing integral with a bottom surface of a laryngoscope spatula. The blade is easily attachable and detachable from a standard laryngoscope handle containing a battery pack and axial pin for engagement with the blade's latch. The bulb is easily threaded into the base housing through a central channel and is removable for replacement by turning the bulb's ribbed base protruding from below the base housing. A bundle of light conducting fibers enclosed within a metal sheath transmit light from the housing to a position near the end of the laryngoscope spatual.

2 Claims, 2 Drawing Sheets

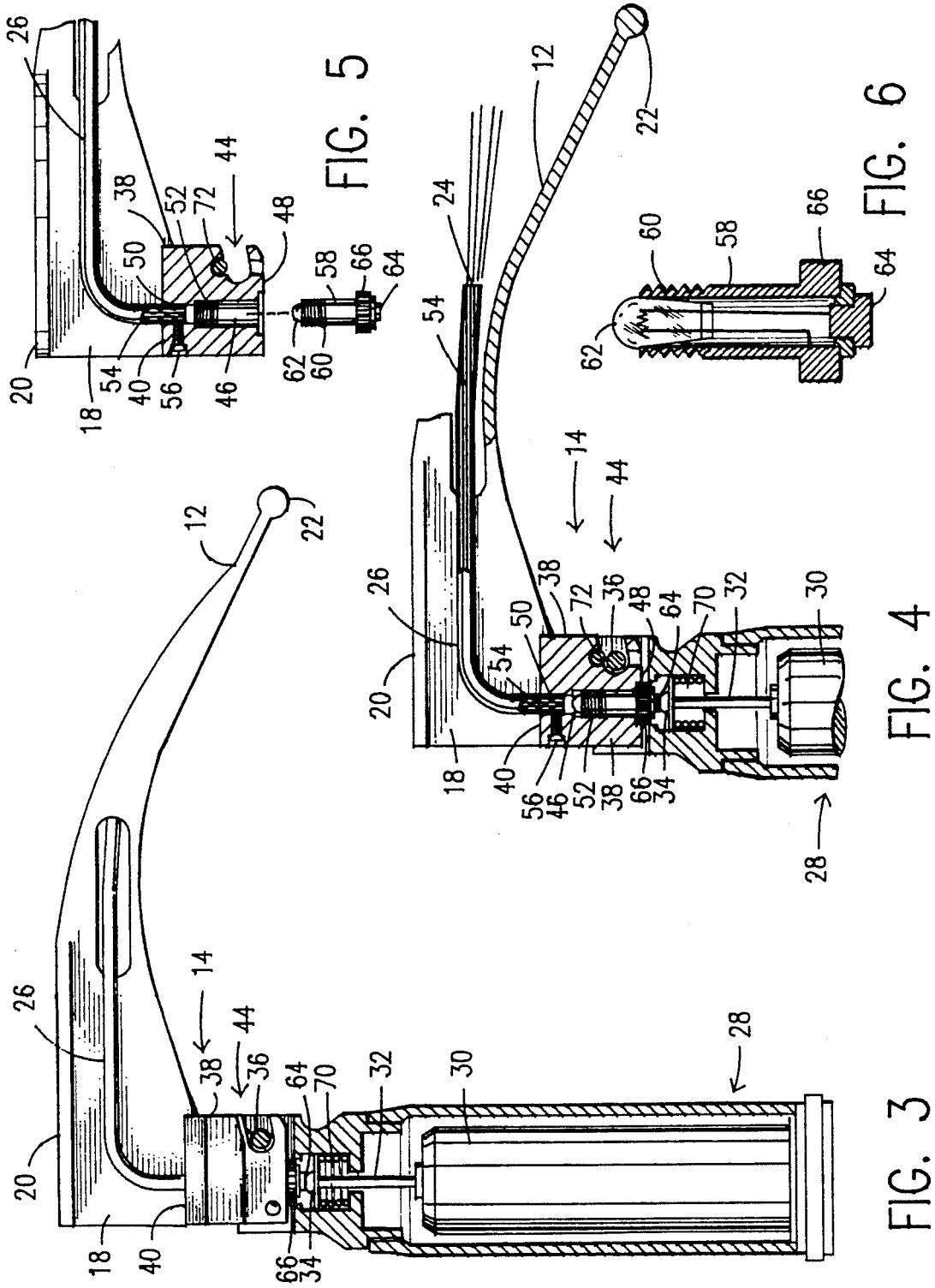

LARYNGOSCOPE BLADE

BACKGROUND OF THE INVENTION

1. Field of The Invention

This invention relates to laryngoscope blades. More particularly, it refers to a laryngoscope blade having a halogen light source in its integral base and a fiber optic cable leading from the light source towards the end of the blade.

2. Description of The Prior Art

In early laryngoscope blades, the light source was supported by and formed part of the blade at a position near the tip of the blade. An example of this type of arrangement is set forth in U.S. Pat. Nos. 3,426,749 and 3,856,001. Unfortunately, it was found that the bulb on the blade generated heat and this caused discomfort to the patient. In addition, the blade had to be cleaned and sterilized and this procedure sometimes damaged the bulb. Through the use of fiber optics, more recent laryngoscope blades have merely had a fiber optic sheath carrying bundles of light conducting fibers from a base of the blade to an end point located above the upper surface of the tongue depressor portion of the blade as shown in U.S. Pat. No. 4,273,112. In this type arrangement, the bulb is located in the handle which is connected by a latching mechanism to the laryngoscope blade. This apparatus worked satisfactorily. However, having a light source bulb conveniently located on the blade separate from the power producing handle is still preferred by many physicians, as long as the bulb will not injure the patient and can be easily removed for sterilization of the blade.

Such a convenient apparatus for location of a bulb in a base portion of a laryngoscope blade is needed.

SUMMARY OF THE INVENTION

I have invented an improved laryngoscope blade containing a self contained light source which allows the user to readily change the light bulb and permit sterilization of the blade without damage to its light producing components.

My improved blade has a base housing integral with a bottom surface of a tongue depressor portion of the blade. This housing has a bulb receiving channel directed upwardly from a bottom wall. The channel narrows adjacent a top wall to receive a bundle of light conducting fibers enclosed within a tubular sheath. The sheath is held in place in the channel with a set screw. The channel has a threaded inner wall to receive complimentary threads from a bulb enclosure. The base housing has a cut out portion on a front wall to accept an axial mounting pin from a laryngoscope handle. The bulb enclosure has a ribbed ring at a bottom portion for grasping and turning to remove the bulb from the housing channel.

BRIEF DESCRIPTION OF THE DRAWINGS

The invention may be best understood by those having ordinary skill in the art by reference to the following detailed description when considered in conjunction with the accompanying drawings in which:

FIG. 3 is a side view in elevation of the laryngoscope blade electrically engaged with its handle.

FIG. 4 is a partial section view of the connection area between the laryngoscope blade light source and the power source.

FIG. 5 is a partial section view of the portion of the laryngoscope blade about to receive its halogen light bulb.

FIG. 6 is a section view of the light bulb and its enclosure used to engage threads in the laryngoscope blade base.

DETAILED DESCRIPTION OF THE INVENTION

Figure 1:
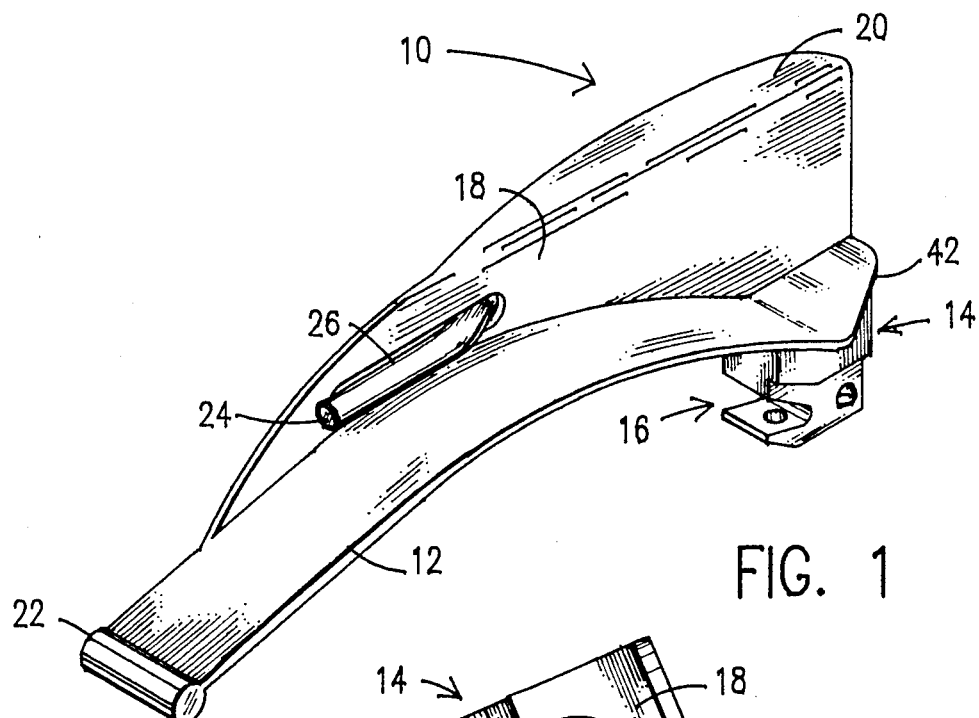
FIG. 1 is a perspective view of the laryngoscope blade of this invention.

Throughout the following detailed description, the same reference numerals refer to the same elements in all figures.

Figure 2:
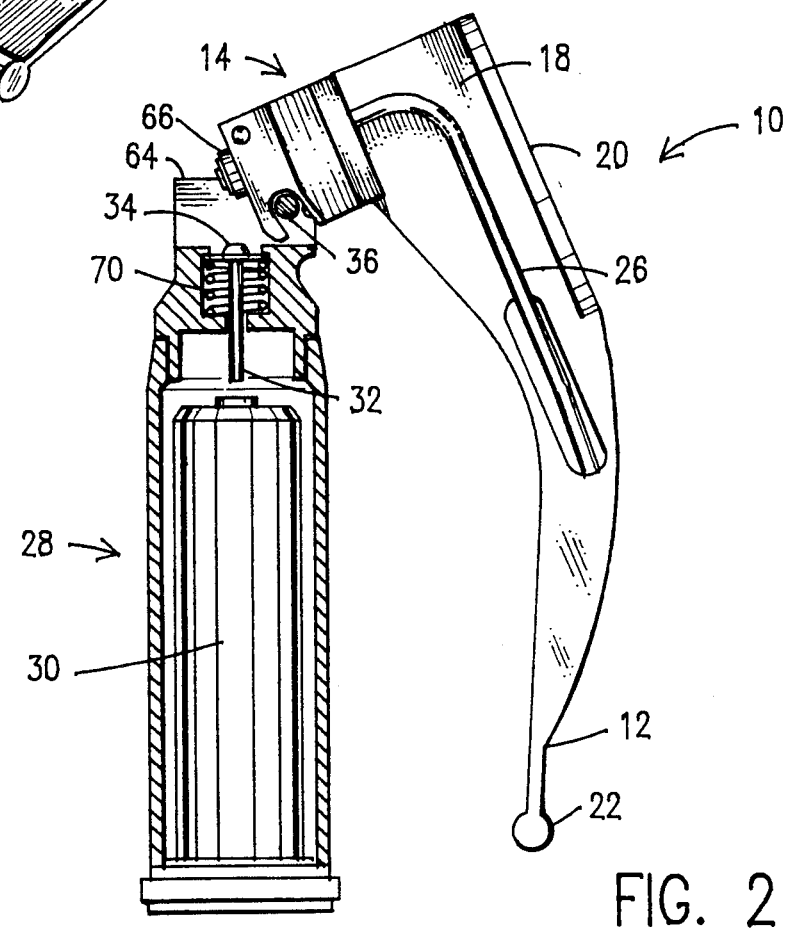
FIG. 2 is a side view in elevation of the laryngoscope blade latched to its handle power source shown in section.

The laryngoscope blade 10 shown in FIG. 1 is a typical Macintosh blade having a tongue depressor 12, a base housing 14 containing a latch mechanism 16, an upright sidewall 18 integral with an edge of tongue depressor 12 and a flat top surface 20. In addition, there is a bead 22 at the end of tongue depressor 12 to prevent injury to the patient. A light outlet 24 terminates a sheath 26 containing a bundle of light conducting fibers 54. The sheath 26 passes through sidewall 18 and is partially located above the tongue depressor 12 as seen in FIG. 1. As seen in FIG. 2 a laryngoscope blade 10 is usually latched to a handle 28 containing a battery 30, contact pin 32 and a handle contact 34. An axial pin 36 mounted o the handle 28 accommodates the latch 16 from the laryngoscope blade 10. Ball bearing 72 assists in the latching.

In the improved laryngoscope blade of this invention shown in FIG. 4, the base housing 14 has four side walls and a top wall 40 integral with a bottom surface 42 of the tongue depressor 12. The front wall 38 has a cut out portion 44 to accommodate the axial pin 36 from the handle unit. A channel 46 is drilled through a bottom wall 48 of the housing 38 and exits through the top wall 40. The channel internal walls have internal threads 52. The channel narrows at a top portion 50 to accommodate the sheath 26 containing the bundle of light containing fibers 54. The sheath 26 is held in place in the channel by screw 56. The sheath 26 continues along the sidewall 18 of the blade 10 and exits within a hole in the sidewall to end in a position above the tongue depressor 12.

A bulb enclosure 58 has external threads 60 enclosing a halogen lamp 62 which has a base contact 64, a ribbed finger grip 66 along a bottom portion just above the bulb contact 64. The bulb enclosure 58 is inserted into channel 46 and the ribbed finger grip 66 is turned in a clockwise direction to seat the bulb within channel 46.

The laryngoscope blade is latched onto axial pin 36 and pressed down upon the contact 34 found on the standard handle. This contact presses a spring 70 and permits the contact pin 32 to contact the battery 30 within the handle. Electrical energy then lights the bulb 62 and the light conducting fibers carries the light to the point of use 24 above the tongue depressor 12.

The surfaces described for convenience in this invention are described as shown in the drawings. It is recognized that the tongue depressor when inserted into the mouth of the patient is inserted in such a fashion that the top surface 20 of the blade faces downward in the patient's mouth.

The blade used in this invention is made of a high strength stainless steel or chrome plated brass. It can be easily sterilized without harm to the materials. It is advisable the bulb be unscrewed prior to sterilization so that electrical failure does not occur. The bulb can be easily re-inserted after sterilization.

Having thus described the invention, what is claimed and desired to be secured by Letters Patent is:

1. In a laryngoscope blade having a self-contained light source, a tongue depressor portion having a first and second end, a blade side wall mounted upwardly along a first edge of the tongue depressor, a light conducting fiber enclosing sheath ending on a top surface of the tongue depressor and the blade being readily connectable and detachable form a handle power source, the improvement comprising, a base housing integral with a bottom surface of the tongue depressor at the first end of the tongue depressor, the housing having four side walls, a bottom wall, and a top wall, the base housing having a bulb receiving channel directed upwardly form the bottom wall, the channel narrowing adjacent the top wall to receive a bundle of light conducting fibers enclosed within a tubular sheath, a portion of the sheath in the channel held in place by a set screw, the channel having threaded inner side walls to receive complimentary threads from a bulb enclosure, a front side wall of the base housing having a cut out portion to accept an axially mounted pin from a laryngoscope handle, and the bulb enclosure having the complimentary threads on an upper portion and a ribbed ring at a bottom portion projecting at least partially below the housing bottom wall, the ribbed ring being used for grasping by a user's finger to insert or remove the bulb from the channel by a turning motion and a contact surface on the bulb below the ribbed ring projecting below the base housing bottom wall to directly complete electrical contact with the handle power source.

2. The improved laryngoscope blade according to claim 1 wherein the bulb within the bulb enclosure is a halogen bulb.

* * * * *